US006588587B2

(12) United States Patent
Johnson et al.

(10) Patent No.: US 6,588,587 B2
(45) **Date of Patent: *Jul. 8, 2003**

(54) PACKAGING SYSTEM FOR MEDICAL COMPONENTS

(75) Inventors: Jeffrey P. Johnson, Boulder, CO (US); Peter S. Jacobson, Lafayette, CO (US); Joseph H. Stoneburner, Loveland, CO (US)

(73) Assignee: COBE Cardiovascular, Inc., Arvada, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/008,390

(22) Filed: Nov. 6, 2001

(65) Prior Publication Data

US 2002/0053528 A1 May 9, 2002

Related U.S. Application Data

(63) Continuation of application No. 09/469,965, filed on Dec. 21, 1999, now Pat. No. 6,311,838.

(51) Int. Cl.[7] .............................................. A61B 19/02
(52) U.S. Cl. ........................ 206/363; 206/438; 206/564
(58) Field of Search ................................ 206/363, 372, 206/373, 438, 564; 220/521, 523, 528, 735

(56) References Cited

U.S. PATENT DOCUMENTS 3,851,649 A * 12/1974 Villari ........................ 206/223
4,523,692 A 6/1985 Lemkin
4,697,703 A * 10/1987 Will ........................... 206/363
4,736,850 A * 4/1988 Bowman et al. ............ 206/370
4,807,747 A 2/1989 Hadtke
4,850,504 A 7/1989 Gindrod et al.
5,031,768 A * 7/1991 Fischer ....................... 206/364
5,085,317 A 2/1992 Jensen et al.
5,148,920 A 9/1992 Walker
5,244,087 A 9/1993 Hikake et al.
5,392,918 A 2/1995 Harrison
5,398,908 A 3/1995 Kienle
5,419,451 A 5/1995 Bitel, Jr.
5,494,162 A 2/1996 Treace et al.
5,507,385 A 4/1996 Koloski et al.
5,520,939 A 5/1996 Wells
5,553,712 A 9/1996 Tisbo et al.
5,738,241 A 4/1998 McEntee
5,795,604 A 8/1998 Wells et al.
5,971,152 A * 10/1999 Bowsman ................... 206/370
6,311,838 B1 * 11/2001 Johnson et al. ............. 206/363

* cited by examiner

*Primary Examiner*—David T. Fidei
(74) *Attorney, Agent, or Firm*—Popovich & Wiles, P.A.

(57) ABSTRACT

An integrated package suited to the packaging of medical devices and surgical equipment including devices and equipment used in heart by-pass surgery has a container and a snap-fit lid. The container and the lid have topographies suitable to conform to the medical components in the container and hold them securely. The lid has first and second grooves which engage a projection on the container and permit the lid to be used in a shipping orientation and a disposal orientation.

6 Claims, 8 Drawing Sheets

PACKAGING SYSTEM FOR MEDICAL COMPONENTS

This is a continuation of application Ser. No. 09/469,965, filed Dec. 21, 1999, now U.S. Pat. No. 6,311,838, the contents of which are hereby incorporated herein by reference.

FIELD OF THE INVENTION

This invention relates to the packaging of medical components. More particularly, this invention relates to sterile packages of medical equipment and devices used in heart surgery.

BACKGROUND OF THE INVENTION

Various sterile packages are used to hold medical components (i.e., devices and equipment) or instruments for surgical procedures. One type of packaging is a molded or thermo-formed sterilized substantially rigid plastic container capable of holding various components. Another type is a flexible pouch into which equipment and supplies can be inserted. The necessary supplies and equipment for a particular surgery are packaged together, sterilized, and delivered to the operating room ready for use.

The current method of packaging oxygenators (i.e., equipment to substitute for lung function during heart by-pass surgery) typically is "bagging" the device in a flexible permeable bag. The device in the bag may be supported by formed plastic within the bag. Supports outside the bag may also used. Such include formed or die-cut foam, die-cut corrugated paperboard, or formed plastic. The flexible permeable bag seals in the oxygenator and acts as a sterile barrier. However, maintaining a sterile barrier with a flexible bag is difficult for a device such as an oxygenator, which may weigh as much as about 6 lb. (2.7 kg), and which contains multiple sharp protrusions (e.g., ports, stopcock manifolds, and mating edges of rigid plastics). Moreover, a flexible bag functions poorly in distributing forces of the oxygenator within the bag, creating pressure points vulnerable to vibrational friction and shock. In addition, the bag can be damaged during handling (before surgery) when the bag and its contents are removed from its shipping container.

Oxygenators are part of perfusion systems used in heart surgery. Similar packaging issues have arisen for perfusion equipment other than oxygenators. Perfusion systems typically contain one or more of an oxygenator, tubing sets, filters, blood reservoirs, sensors, connectors, blood cooling coils and other items comprising an extracorporeal blood circuit that may be used in heart by-pass procedures.

A technician assembles and packages the components of a perfusion system to the specifications of a particular hospital, typically as defined by the surgical team. Thus there are a variety of types of such packages on the market and the components of these packages may very greatly. For example, in addition to the variability in the number and type of components present in the package, the components may be connected in a sequence and with varying lengths of tubing as specified by the surgical team. It is frequently desirable to provide the packages "pre-connected", so that very little, if any, set up of the packaged components is required.

One currently available perfusion package is a rigid thermoformed container with a rigid inner tray securely taped within the container. The inner tray holds the necessary components and devices of the perfusion package by various shaped holders, adhesive tapes, and fasteners. The container is sealed with a breathable covering, such as a polyethylene membrane (such as that commercially available under the trade designation TYVEK™ from E.I. DuPont deNemours and Co.). A breathable covering permits sterilization of the package with ethylene gas.

Another commercial product is a two-tiered system having a rigid thermoformed plate separating the tubing sets on the bottom tier of a rigid container from the oxygenator and pump lines on the top tier. The contents of the package are secured by using shrink-wrap film. The entire tray is covered with sterile surgical paper and sealed in a breathable bag. The system is sterilized and then shipped to the customer.

Yet another packaging system is a semi-rigid corrugated plastic tray that has metal framing to provide added support to the tray. Devices and components are strapped within holders or formed parts that are adhered to the floor of the tray and secured with mechanical fasteners. Once the tray has been packed, it is covered with a corrugated plastic lid. The entire system is placed into a breathable sterile barrier bag for sterilization before use.

Current packaging systems share some disadvantages. Current systems typically are packed to each customer's specifications so each package may have different components in it. There is no defined position in the package for a component. Typically the technician who is packing perfusion equipment loads in the medical components and restrains them from movement by means of various fasteners. Because of this, the systems are not only time-consuming to pack but operator inconsistencies develop because of variable placement of the components. These disadvantages also lead to more costly assembly time.

Disposal of the package, once the components in the package have served their use in surgery, can also be problematic. Typically, the components and the package are placed in bags or pouches for removal and disposal. This also is an additional expense and can be time consuming.

Thus, a need in the art exists for a packaging system for medical components which provides ease of assembly and use, adequate support and cushioning for the components, the ability to vary the types of components without changing the package, and a way to dispose of the package inexpensively and conveniently.

SUMMARY OF THE INVENTION

This invention is an integrated package particularly suited to the packaging of medical devices and surgical equipment including devices and equipment used in heart by-pass surgery. The package comprises a container and a snap-fit lid. The lid is positioned in the opening of the container and pushed into position. A projection on the container and a groove on the lid provides a "snap-fit" of the lid to the container.

In a first aspect, this invention is a packaging system for medical components comprising a container having a bottom surface, first and second opposing sidewalls and third and fourth opposing sidewalls, the bottom surface and sidewalls being connected to form an interior surface of the container such that an opening is formed in the container opposite the bottom surface, the opening being defined by a top edge of the sidewalls, the sidewalls having a circumferential projection in the direction of the interior surface; and a lid having a first side and a second side and a perimeter section sized to fit within the opening in the container, the perimeter section having at least one circumferential groove, the lid being configured to attach to the container in a manner that covers the opening in one of a first mode where the second side of the lid is oriented toward the interior surface of the container and a second mode where the first side of the lid is oriented toward the interior surface of the container, the at least one groove being configured to accommodate the projection when the lid is attached in the first mode and when the lid is attached in the second mode.

The circumferential projection may be continuous and the groove may be continuous. In a preferred embodiment, there are two grooves on the lid. In another preferred embodiment, one of these grooves is continuous and the other groove is provided with at least one channel. Preferably, the projection is substantially parallel to the top edge of the sidewalls and the projection is located adjacent the top edge of the sidewalls. When the lid is attached in the first mode, the interior surface of the container and the second side of the lid define a first enclosed volume and when the lid is attached in the second mode, the interior surface of the container and the first side of the lid define a second enclosed volume wherein the first volume is less than the second volume.

In a second aspect, this invention is a packaging system for medical components comprising a container having an interior surface and an opening; a lid configured to attach to the container in a manner that covers the opening, the lid having a shipping side and a disposal side; and means for attaching the lid to the container such that the lid may be attached to the container with the disposal side facing the interior surface or with the shipping side facing the interior surface.

In a third aspect, this invention is a packaging system for medical components comprising a container having a bottom surface, and sidewalls including first and second sidewalls, the bottom surface and sidewalls being connected such that an opening in the container is formed opposite the bottom surface, the first and second sidewalls including at least one rib; a lid configured to cover the opening in the container; and an insert configured for mounting on one of the first and second sidewalls, the insert having a surface configured to be securely affixed to the rib of the first sidewall when the insert is mounted on the first sidewall and to be securely affixed to the rib of the second sidewall when the insert is mounted on the second sidewall.

Preferably, the insert is removably secured to the at least one rib. The rib may have a V-shape. The insert may be a folding plate. The lid may have a topography adapted to conform to the shape of the medical components in the container and the insert may have a topography adapted to conform to the shape of medical components held by the insert.

In a fourth aspect, this invention is a packaging system for medical components, comprising a container having an interior surface and an opening; a lid configured to attach to the container in a manner that covers the opening; and means for securing the medical components within the container.

In a fifth aspect, this invention is a packaging system for medical components comprising a container having an interior surface and an opening, the interior surface having first and second protrusions; a lid configured to attach to the container in a manner that covers the opening; and an insert configured for selective mounting in multiple locations within the container including adjacent one of the first and second protrusions, the insert having a surface configured to be securely affixed to the first protrusion when the insert is mounted adjacent the first protrusion and to be securely affixed to the second protrusion when the insert is to be mounted adjacent the second protrusion.

In a sixth aspect, this invention is a method of packaging medical components comprising supplying a packaging system including a container having an interior surface and an opening, the interior surface having at least one protrusion, a lid configured to attach to the container in a manner that covers the opening, and an insert having a surface configured to connect with the at least one protrusion and to conform to the surface contour of a medical component; placing a medical component within the container with a surface contour of the medical component conforming to the surface of an insert which is connected to the protrusion; and attaching the lid to the container to secure the medical component within the container.

In a seventh aspect, this invention is a method of disposing of used medical components comprising supplying a packaging system for shipment of the medical components, the packaging system comprising a container having an interior surface and an opening, and a lid configured to attach to the container in a manner that covers the opening in both a shipping mode in which a first side of the lid faces the interior surface and a disposal mode in which a second side of the lid faces the interior surface; placing the used medical components in the container in which they were shipped; covering the container with the lid oriented in the disposal mode such that the second side of the lid faces the interior surface.

DETAILED DESCRIPTION OF PREFERRED EMBODIMENTS

Figure 1:
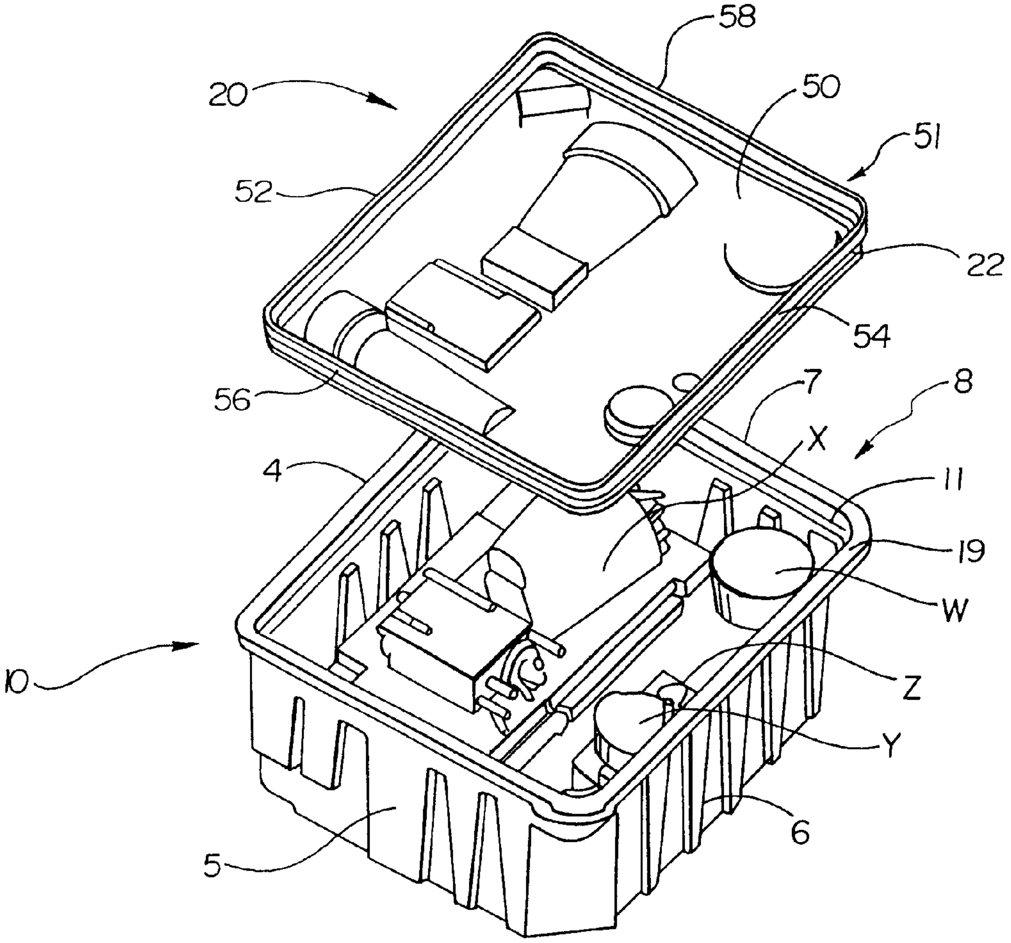
FIG. 1 is an exploded perspective view of a first embodiment of the lid and container of the packaging system of this invention with medical components shown housed in the container.

This invention is a packaging system particularly suited to the packaging of medical components such as medical devices and equipment used in surgery. In a preferred embodiment, the packaging system contains devices and equipment comprising an extracorporeal blood circuit used in heart by-pass surgery. The packaging system comprises a container and a snap-fit lid. The container is provided with a projection that matingly engages with a groove on the snap-fit lid. Alternately, a groove on the container could matingly engage with a projection on the lid. The container is designed to hold various medical components, including one or more of oxygenators, tubing sets, filters, blood reservoirs, sensors, connectors, and blood cooling coils. The components may be joined together by tubing, i.e., pre-connected, for immediate use in surgery. The packaging system minimizes the use of tapes and straps to restrain the medical components from movement and preferably omits the use of tapes and straps.

In a preferred embodiment, first and second parallel grooves on the snap-fit lid are designed to engage with the projection on the container depending on the orientation of the lid. When a first groove engages the projection, the packaging system is in shipping mode. When the second groove engages the projection, the system is in disposal mode. The second groove is designed so that it is very difficult to remove the lid once it has been placed on the container in its disposal mode.

Any suitable inert, sterilizable material may be used to form the packaging system of this invention. Preferably, the container and the lid are each formed from plastic materials to a desired shape, size, and topography. Formed plastic materials include, for example, thermoformed and injection molded polymers. Suitable plastic materials for use in this invention include, for example, polyethylene, polyester, polycarbonate, polyethylene terephthlate, polystyrene, and polyvinylchloride.

The lid and container are manufactured to any desired dimension. A typical packaging system for perfusion equipment may be, for example, about 30 inches wide by 24 inches long by 13 inches high (76 cm by 61 cm by 33 cm).

The lid and the container are designed to hold various components and may have cavities, recesses, partitions, or other features formed into them, producing the desired topography for the system, as described further below. Alternatively, other features can be added to the container or to the lid by use of adhesives or by sonic welding. Preferably, at least some of the medical components are held securely in the container by means of one or more removable inserts. The molded inserts may fit along a sidewall, at a corner, or on the bottom of the container. They can be used as necessary to hold various components. It is preferred that the medical components are held securely in the container by fitting components into designed recesses. This is important particularly after medical components have been pre-connected. In this way, they are ready for use when the container is opened. However, they may alternatively, or additionally, be secured by adhesive, adhesive tapes, mechanical fasteners, and the like. Mechanical fasteners preferably include hook and loop fasteners such as those commercially available under the trade designation VELCRO™ fasteners.

Medical components and devices are placed into the container in a desired arrangement and the lid is positioned onto the container. A permeable "lid-stock" or membrane, such as a permeable high density polyethylene is affixed to the container, typically by heat sealing with a platen. A suitable and conventionally used permeable, as well as tear resistant, material is a polyethylene commercially available under the trade designation TYVEK™ from DuPont.

The packaging system is sterilized by exposing the container to a sterilizing gas, such as ethylene oxide, or to gamma radiation, as is known to those of skill in the art. Sterilizing gas passes through the permeable membrane and into the container. If ethylene oxide is the sterilization method used there may be channels or interruptions in the groove that engages with the projection so that gas may flow through. The lid of the container may be provided with passages or throughways so that gas can flow into the container. After sterilization, the packaging system is placed in a container such as a cardboard box and shipped to the user.

Figure 2A:
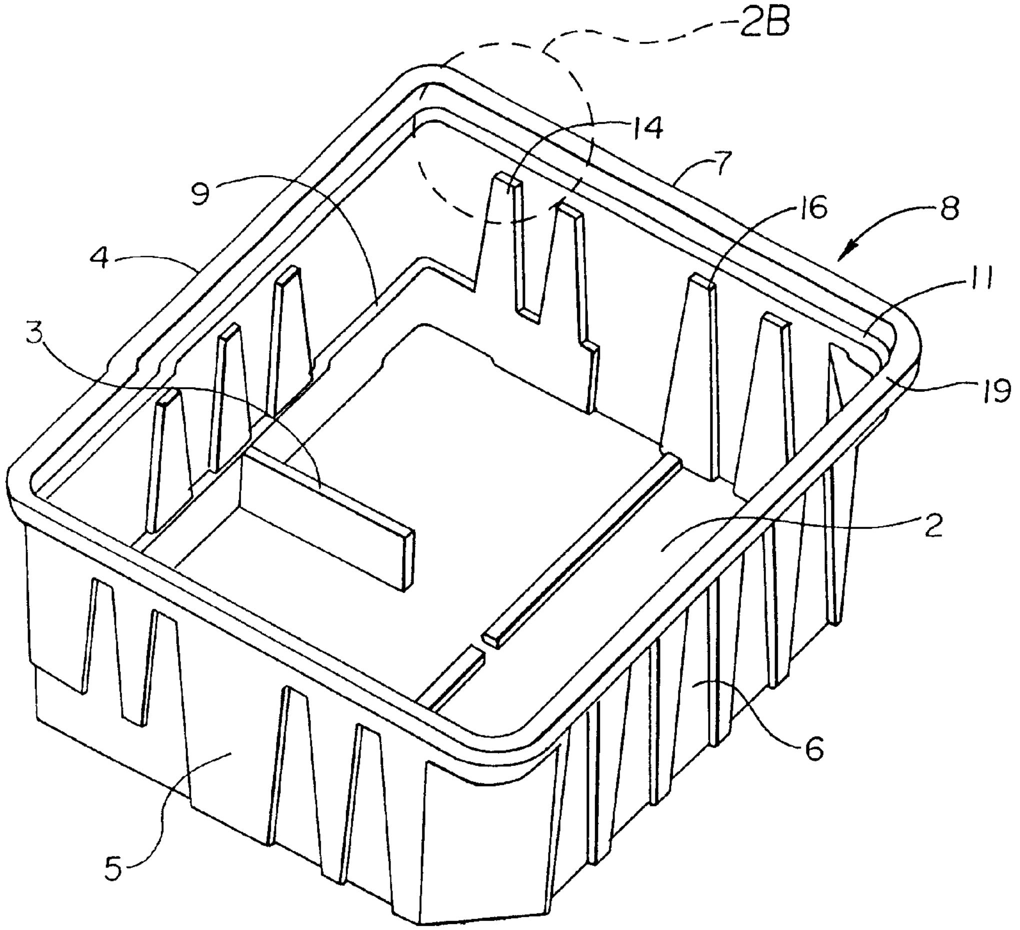
FIG. 2A is a perspective view of the container of FIG. 1

Turning now to the Figures, the features of the packaging system are described in detail. FIGS. 1 and 2A illustrate a perspective view of container 10, medical components W, X, Y, and Z in container 10, and lid 20. Container 10 is formed from bottom surface 2, opposing sidewalls 4 and 6, and opposing sidewalls 5 and 7. The bottom surface and the sidewalls form an interior surface and define a space that holds medical components. The sidewalls join each other; the top edges of the sidewalls define opening 8 opposite bottom surface 2. Facing the interior of and near the opening of container 10 is projection 11. Projection 11 may be continuous about the circumference of the inside of container 10 or it may be interrupted, for example, at the corners. The projection can be located any distance from the top of the container. FIG. 1 illustrates a projection located about 0.5 inches (1.2 cm) from the opening. Typically, it is desirable to maximize the space within the container. Projection 11, as seen in cross-section in FIGS. 7A and 7B, has portion 13 substantially perpendicular to the plane of the sidewall of container 10 and portion 15 disposed at an angle relative to the plane of the sidewall.

In an alternate embodiment of the packaging system, the container may be provided with more than one projection. A projection nearest the top opening would be used to engage a groove on a lid. Another projection could be located on one or more walls of the container farther away from the top opening. This projection could be used to engage a groove on a plate or a divider. In this way, a partial or full plate or divider could be positioned within the container. For example, a horizontal plate or divider could be positioned in the container using a projection in the container to engage with a groove on a plate or divider.

Container 10 also has sealing flange 19 disposed about opening 8. The sealing flange permits heat-sealing of a permeable membrane (not shown) over the top of the lid once the components are loaded into the container.

Lid 20 may be provided with various shapes or contours which conform to the shape of the medical components in the container to facilitate holding the components in the container as described further below. Lid 20 has major surfaces or sides 50 and 51 and sidewalls 52, 54, 56, and 58. The perimeter of lid 20 is sized to fit within the opening in the container. The shipping mode of the container is shown with major surface or side 50 facing upward in FIG. 1 and major surface or side 51 facing downward, into the interior of container 10. Lid 20 is provided with groove 22 along the outside perimeter, i.e., the circumference, of the lid sidewalls 52, 54, 56, and 58. Groove 22 engages projection 11 when the lid is pushed onto the container. The preferred orientation for lid 20 is as shown in FIG. 1, with major surface 50 facing upward. A less preferred orientation (not shown) for lid 20 has major surface 51 facing upward, thus providing greater volume of the packaging system, useful for the disposal orientation of the system.

Figure 2B:
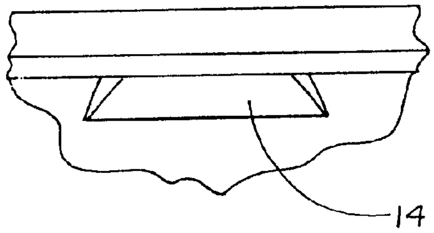
FIG. 2B is a partial top view of the container.

FIG. 2A shows container 10 having sidewalls with various shapes formed or otherwise attached to them. In FIG. 2A, sidewalls 4, 5, 6 and 7 are provided with ridge or step 9, integral with sidewall 4 and portions of sidewalls 5 and 7, and partition 3, integral with sidewall 4 and bottom surface 2. Ridges, partitions, and ribs serve to support various components within the container, as described further below. The ridges, partitions, and ribs in FIG. 2 are intended to be illustrative of the topography of the inside of the container, and are not intended to limit the contours that are useful and can be obtained, as known to those of skill in the art. Sidewall ribs are preferred in the container in order to provide additional structural support to the container as well as to allow various components to be held securely in container 10. Such ribs may have a variety of lengths along the sidewalls as well as various widths and shapes. Preferably, sidewalls 4, 5, 6, and 7 are provided with at least one V-shaped rib such as dovetail ribbing 14 and 16. Ribbing 14 extends from near the top of sidewall 7 and adjoins ledge 9. Ribbing 16 extends from near the top of sidewall 7 to bottom 2. FIG. 2B is a top view of a portion of the container, showing a preferred shape of the dovetail ribbing. Preferably, the ribbing is angled inwardly, toward the sidewalls of container 10, though it may be angled outwardly or be perpendicular to the sidewalls.

Figure 3A:
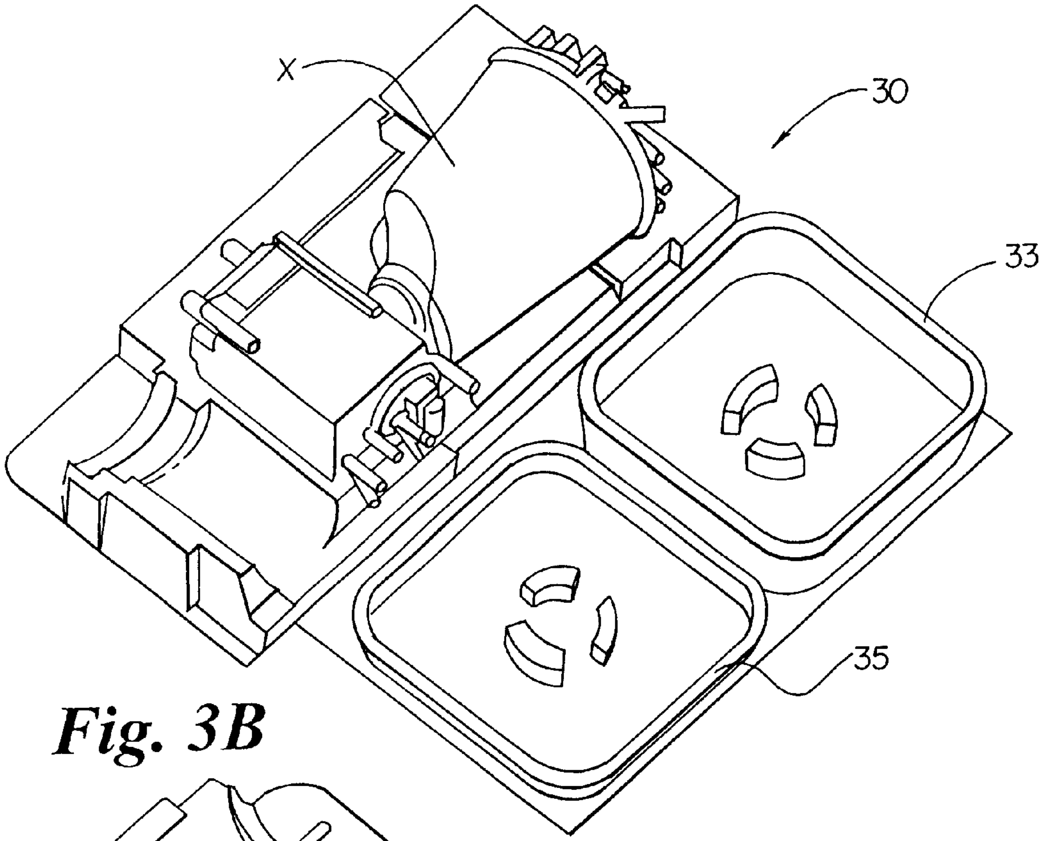
FIGS. 3A and 3B are perspective views of a plate designed to hold various components within the container of FIG. 1.
Figure 3B:
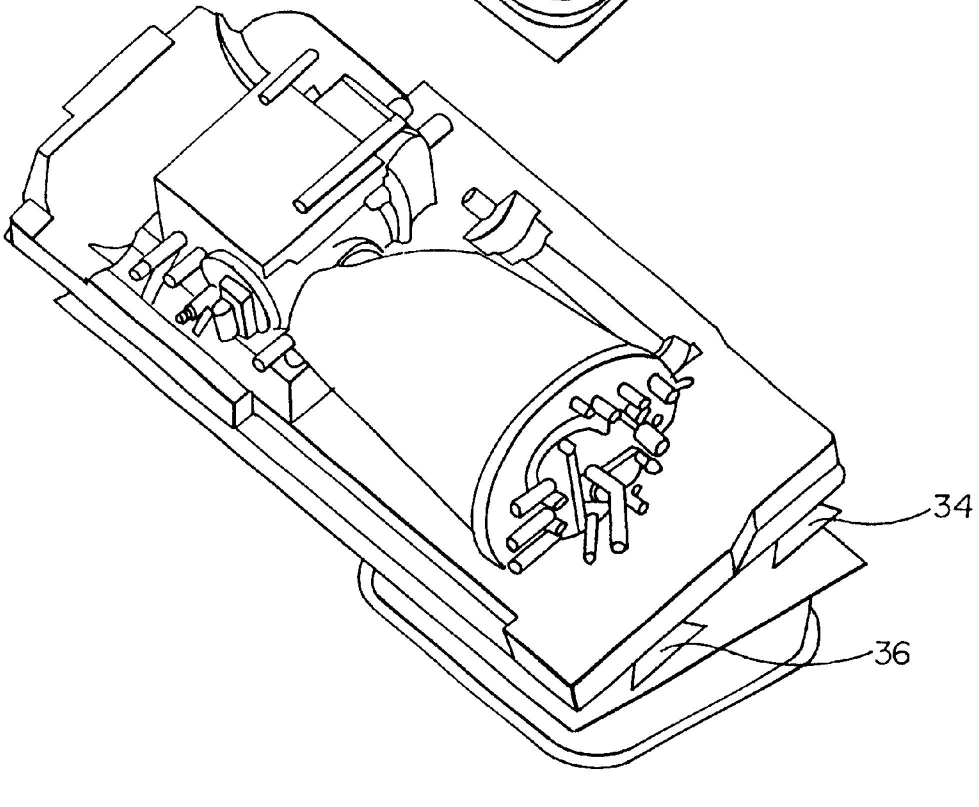

FIGS. 3A and 3B illustrate rigid folding plate 30 which is provided with a geometry useful for mating with various products to be held in container 10. Plate 30 is formed with various features in it in order to support and contain a desired medical component. For example, in FIGS. 3A and 3B, plate 30 is shown contoured to accommodate oxygenator X. Plate 30 is also provided with tabs 34 and 36, which are adapted to fit between the ribbing on the sidewalls of container 10. Plate 30 lies flat, as shown in FIG. 3A, while medical components are loaded into it. Once loaded, plate 30 is folded in half, as shown in FIG. 3B, and placed into container 10. Partition 3 on the bottom surface of the container separates molded protrusions 33 and 35. In addition, the dovetail ribbing 14 and 16 mates with tabs 34 and 36, respectively, along the side of plate 30, thus holding plate 30 firmly in place. Plate 30 also may easily be removed from container 10, if desired. The use of plate 30 avoids the need for mechanical fasteners, tapes, or adhesives.

Figure 4A:
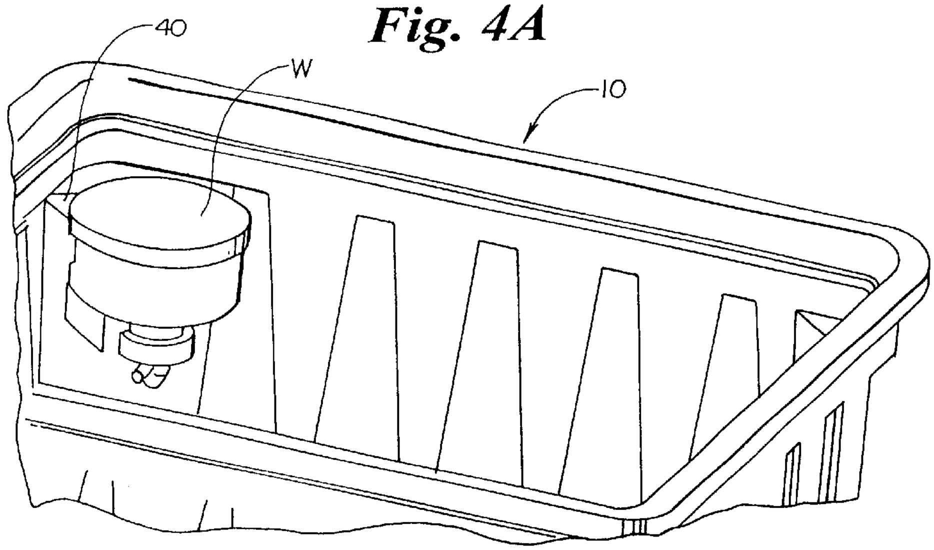
FIG. 4A is a partial view of the container of FIG. 1 illustrating a type of formed insert holding a medical component.
Figure 4B:
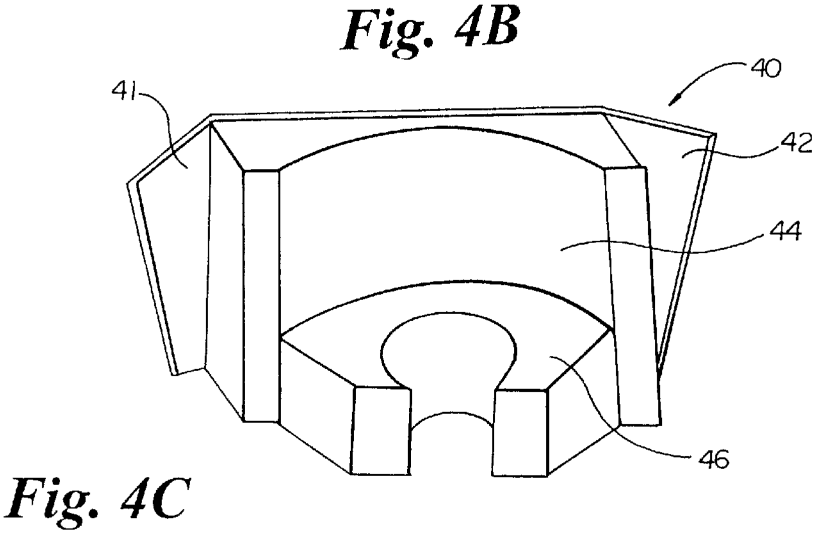
FIG. 4B is a perspective view of the formed insert of FIG. 4A.
Figure 4C:
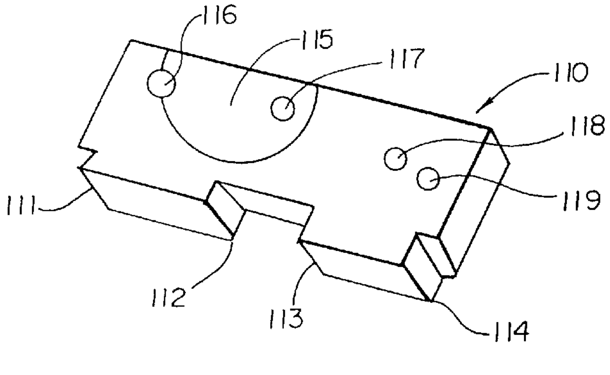
FIG. 4C is a perspective view of another type of formed insert.
Figure 4D:
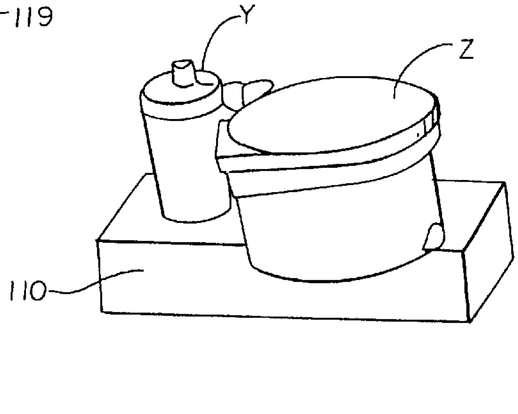
FIG. 4D is a back view of a medical component held by the insert of FIG. 4C.

FIG. 4A shows a perspective view of a portion of container 10 having removable molded insert 40 at a corner holding medical component W, which could be, for example, a blood recovery system. Insert 40 has side flanges 41 and 42 adapted to mate with dovetail ribbing 14 and 16 on the sidewalls. FIG. 4B is a perspective view of insert 40, showing the shape of footprints 41 and 42, concavity 44, and shelf 46. Shelf 46 is shaped to fit the neck of medical component W. FIG. 4C shows another form of molded insert 110 having V-shaped footprints 111, 112, 113, and 114 adapted to mate with dovetail ribbing 14 and 16 on the sidewalls. The topography of molded insert 110 is shaped with circular cut-out 115 and holes 116 to 119 to accommodate medical devices Y and Z (such as, for example, cardioplegia devices) as shown in FIG. 4D. Thus components Y and Z are secured between the insert and the lid once the lid is secured onto the container. As will be appreciated by those of skill in the art, various forms of molded inserts can be configured in order to accommodate and secure the shape of any desired medical device. The mating configuration of the V-shaped footprints and the ribbing serves to secure or lock the insert and hence the component in place.

Figure 5:
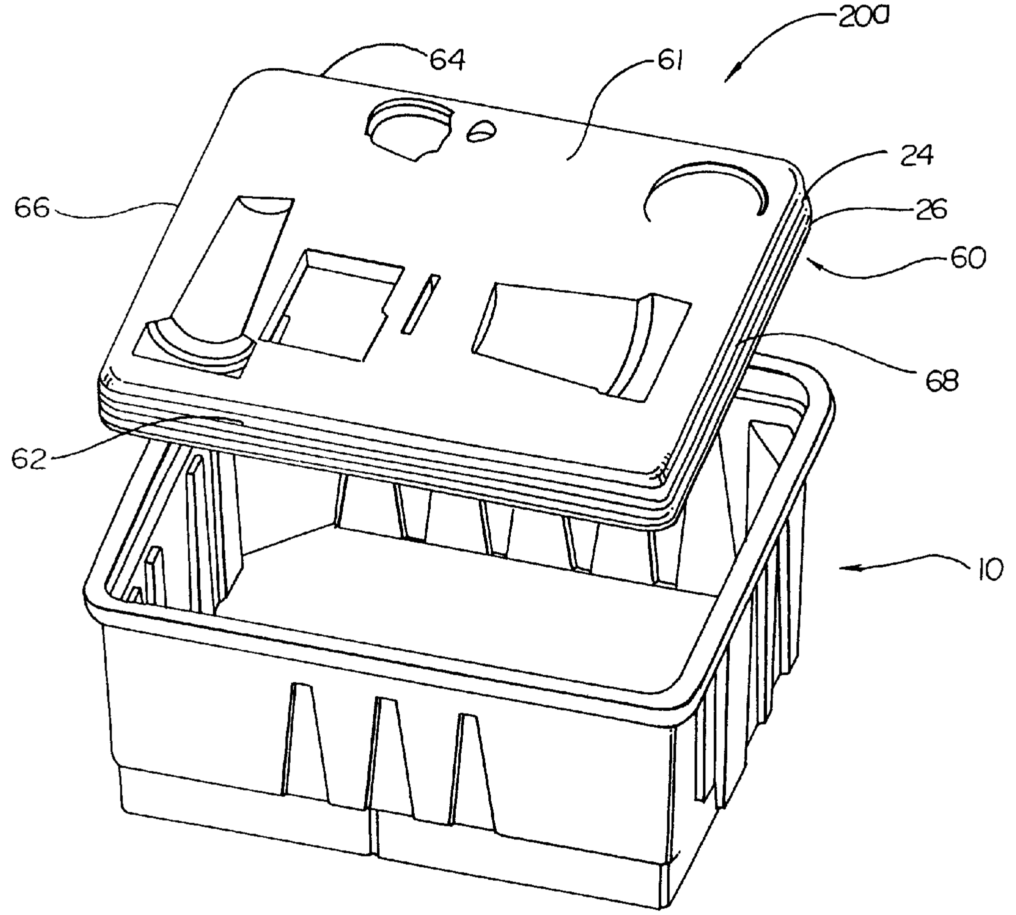
FIG. 5 is a perspective view of a second embodiment of the packaging system of this invention.

FIG. 5 illustrates another embodiment of the invention, similar to the first embodiment except for lid 20*a*. Lid 20*a* is configured to be used in one orientation in a shipping mode and in a second orientation in a disposal mode; that is, one side faces the interior of the container in shipping mode and the other side faces the interior of the container in disposal mode. Lid 20*a* has major surfaces 60 and 61 joined to sidewalls 62, 64, 66, and 68. Two parallel grooves 24 and 26 are disposed along the outside perimeter of lid 20*a*. FIG. 5 shows the disposal orientation of the lid. The topography of the surface of lid 20*a* is designed to match the medical components (e.g., components W, X, Y, and Z) in container 10 that are supported by folding plate 30 and molded inserts 40 and 110 (as illustrated in FIGS. 4A, 4B, 4C, and 4D). In the shipping mode or orientation, first surface or side 60 faces upward and second surface or side 61 faces the container. In the disposal mode or orientation, as shown in FIG. 6B, the lid is flipped over (i.e., inverted or rotated 180°), so that first surface or side 60 faces the container.

Figure 6A:
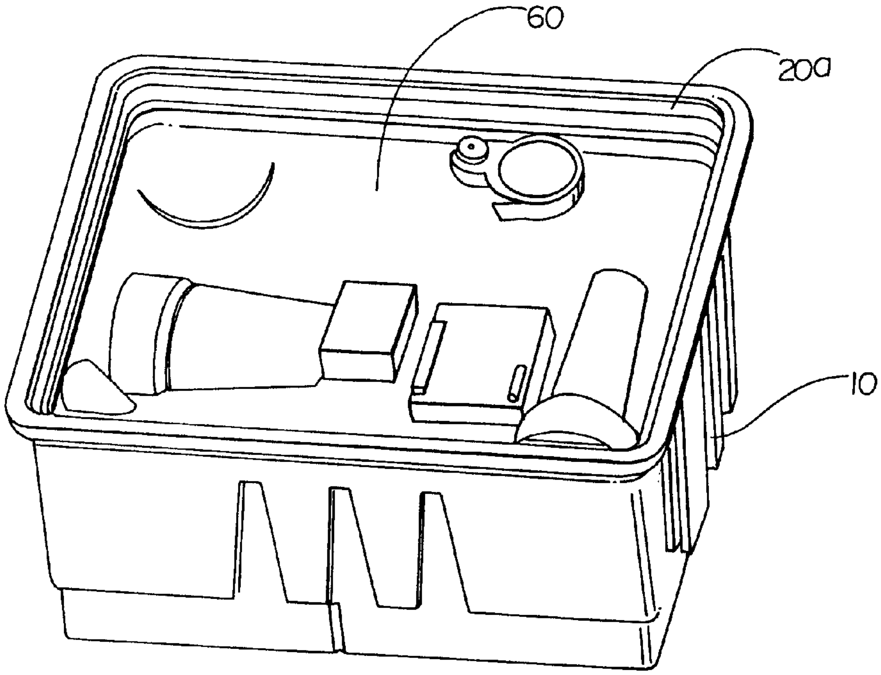
FIGS. 6A and 6B are perspective views of the packaging system of FIG. 5 in shipping mode and disposal mode, respectively.
Figure 6B:
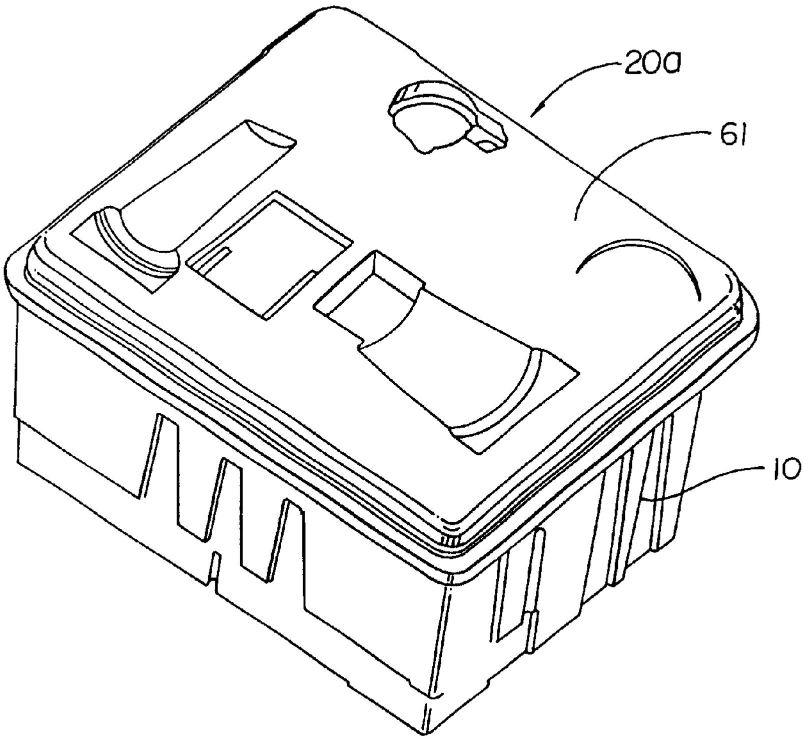
Figure 7A:
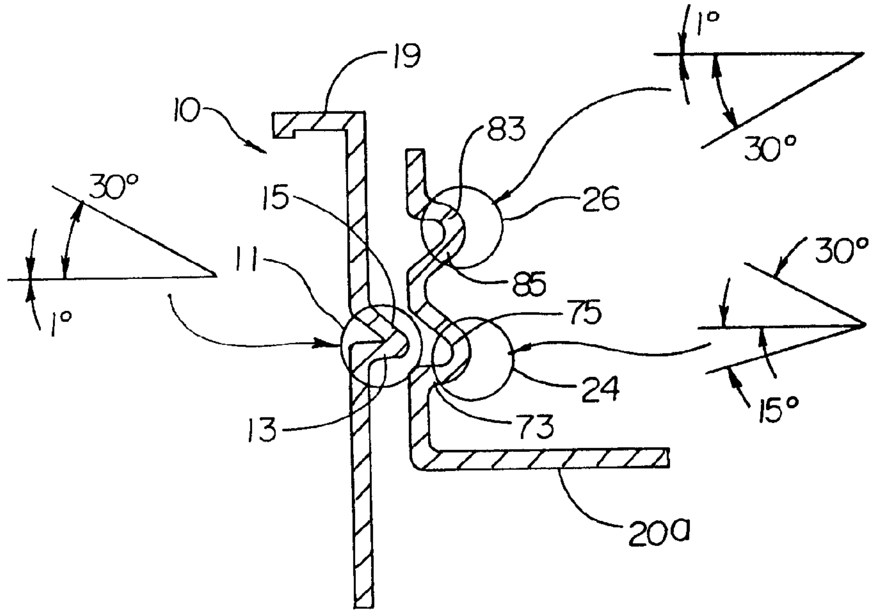
FIGS. 7A and 7B are partial cross-sectional views of the packaging system of FIGS. 6A and 6B, respectively.
Figure 7B:
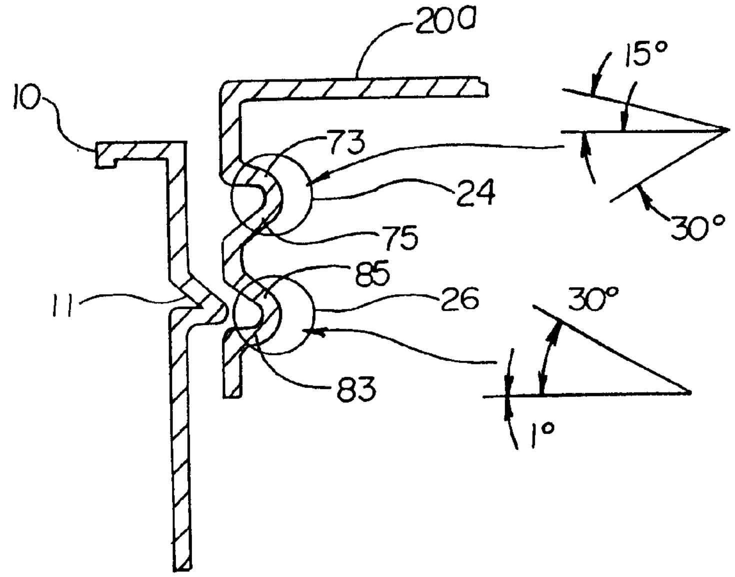

FIGS. 6A and 6B show the shipping and disposal modes of the packaging system, respectively. FIGS. 7A and 7B are partial cross-sectional views of an exploded section of the lid and container showing the orientation and alignment of the projection and the grooves. FIGS. 6A and 7A illustrate the shipping orientation of the package, with first surface 60 facing upward. FIGS. 6B and 7B illustrate the system in disposal mode, with first surface 60 of the lid facing downward, toward container 10, and second surface 61 facing upward.

FIGS. 7A and 7B illustrate the geometry of projection 11 and grooves 24 and 26 in cross-section. Projection 11 has portion 13 substantially perpendicular to the plane of the sidewall of container 10 and portion 15, disposed at an angle relative to the plane of the sidewall. When the packaging system is in shipping mode, first groove 24 engages projection 11 on container 10, as illustrated in FIG. 7A. Groove 24 can be viewed as being comprised of two angled surfaces 73 and 75; that is, neither of these surfaces is substantially perpendicular to the plane of the lid sidewall. This results in a snap-fit when the lid is placed into position over the container, but also results in the lid being removable. The shape of groove 24, in combination with the natural flex of the container sidewalls, allows minimal force to be used when assembling the package.

In contrast, the cross-section of groove 24 is not the same as that of groove 26. Groove 26 can be viewed as comprised of two surfaces 83 and 85. Surface 83 is substantially perpendicular to the plane of the lid sidewall. This results in a tight fitting engagement of the lid on the container when the lid is positioned for disposal mode and much more difficulty in removing the lid.

During shipment, the combination of permeable barrier (sealed to the top perimeter of the container) and a corrugated over-wrap (not shown) prevent excessive flexing of the container sidewalls. The lid-stock and over-wrap also assist in restraining the lid, and thus also restrain the components in the package. In disposal mode, the used medical components are returned to the container, and the lid is placed on the container in a 180° orientation from the shipping mode. This results in a larger volume for the enclosed container, as can be seen in FIGS. 6A and 6B. This is an advantage because the medical components may not be carefully repacked when they are disposed of and greater volume may be necessary. The disposal orientation also produces a vessel for the safe temporary removal of medical waste because the contents inside the container are sealed. The lid is difficult to remove in disposal mode and leakage of fluids is minimized.

A gasket also could be provided on the lid of the packaging system. This would be useful in disposal mode so that the system can be used as a primary vessel for waste disposal.

Figure 8:
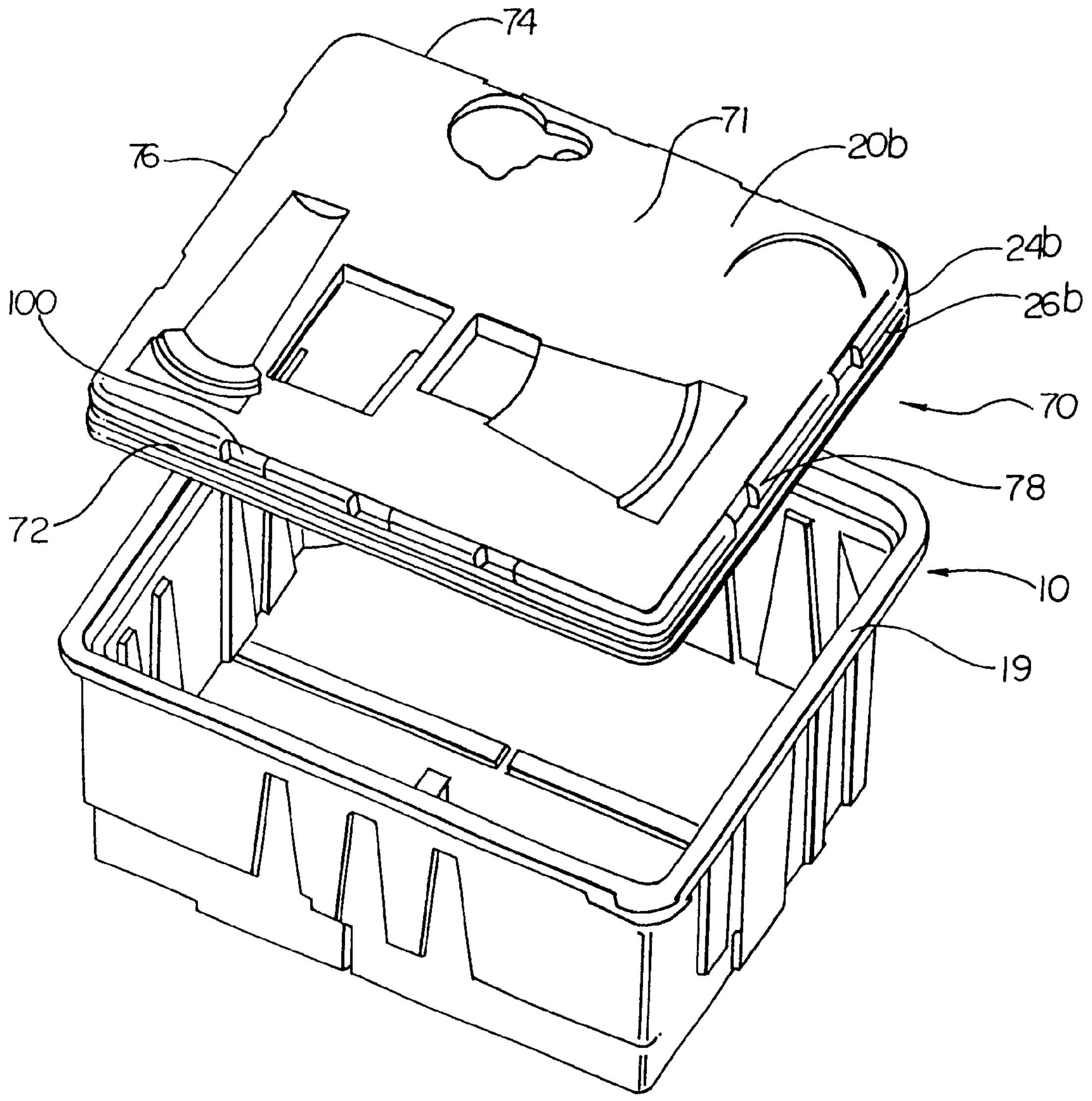
FIG. 8 is a perspective view of a third embodiment of the packaging system of this invention.

FIG. 8 illustrates an alternate embodiment of the packaging system of this invention. Container 10 supports various perfusion equipment. Lid 20*b* has major surfaces 70 and 71 provided with a topography to match the components lying beneath it. Lid 20*b* has sidewalls 72, 74, 76, and 78.

Two parallel grooves 24*b* and 26*b* are provided around the perimeter of lid 20*b*. Groove 24*b* is interrupted by one or more channels 100 disposed around the perimeter of the lid. The channels permit the flow of sterilizing gases (e.g., ethylene oxide) into and out of the container when the lid is in shipping mode, that is, when the lid is positioned on container 10 and groove 24*b* engages projection 11. The channels do not pass through the plane of groove 26*b*, so that when the lid is inverted and groove 26*b* engages projection 11 (the orientation shown in FIG. 8), there can be no leakage of fluid from the container when it is in disposal mode.

Although a particular embodiment of the invention has been disclosed herein in detail, this has been done for the purposes of illustration only, and is not intended to be limiting with respect to the scope of the appended claims. It is contemplated that various substitutions, alterations, and modifications may be made to the embodiment of the invention described herein without departing from the spirit and scope of the invention as defined by the claims.

What is claimed is:

1. A packaging system for medical components comprising:

a container having an interior surface and an opening;

a lid sized to attach to the container in a manner that covers the opening, the lid having a first side and a second side; and means for attaching the lid to the container such that the lid may be attached to the container with the first side facing the interior surface when the container is in a shipping mode used for shipping medical products or with the second side facing the interior surface when the container is in a disposal mode used for disposing of medical products, a first force being required to remove the lid from the container when the container is in the shipping mode and a second force being required to remove the lid from the container when the container is in the disposal mode, the second force being greater than the first force.

2. The packaging system of claim 1 wherein when the lid is attached to the container such that the second side is oriented toward the interior surface of the container the second side and interior surface define a first enclosed volume and when the lid is attached to the container such that the first side is oriented toward the interior surface of the container the first side and interior surface define a second enclosed volume, the second volume being greater than the first volume.

3. The packaging system of claim 1, further comprising means for securing the medical components within the container.

4. The packaging system of claim 3 wherein the means for securing medical components is removable.

5. The packaging system of claim 1 wherein the lid has a topography adapted to conform to the shape of the medical components within the container when the container is in the shipping mode.

6. The packaging system of claim 3 wherein the means for securing the medical components has a topography adapted to conform to the shape of the medical components.

* * * * *